US005622933A

United States Patent [19]
Sabatier et al.

[11] Patent Number: 5,622,933
[45] Date of Patent: Apr. 22, 1997

[54] MULTIPLE BRANCH PEPTIDE CONSTRUCTIONS FOR USE AGAINST HIV

[75] Inventors: Jean M. Sabatier, Chateauneuf de Rouge; Abdelaziz Benjouad, Cachan; Nouara Yahi, Marseille; Emmanuel Fenouillet, La Valette du Var; Kamel Mabrouk, Marseille; Jean-Claude Gluckman, Paris; Jurphaas Van Rietschoten, Aix en Provence; Herve Rochat, Mimet, all of France

[73] Assignee: Armel S.A., Steinsel, Luxembourg

[21] Appl. No.: 260,086

[22] Filed: Jun. 15, 1994

[30] Foreign Application Priority Data

Sep. 13, 1993 [GB] United Kingdom .................. 9318901

[51] Int. Cl.[6] ................................................. A61K 38/04
[52] U.S. Cl. ............................. 514/16; 514/17; 530/324; 530/326; 530/327; 530/328
[58] Field of Search ................................ 530/324, 326, 530/327, 328; 514/12, 13, 14, 15, 16, 17

[56] References Cited

FOREIGN PATENT DOCUMENTS

| 0311219 | 4/1989 | European Pat. Off. . |
|---|---|---|
| 0328403 | 8/1989 | European Pat. Off. . |
| WO92/17590 | 10/1992 | European Pat. Off. . |
| WO92/14489 | 2/1991 | WIPO . |
| WO92/20373 | 11/1992 | WIPO . |
| WO93/03766 | 3/1993 | WIPO . |

OTHER PUBLICATIONS

ARIPO Search report AP/P/94/00680.
Search report for PCT/GB94/01992.
"Multibranched V3 Peptides Inhibit Human Immunodeficiency Virus Infection in Human Lymphocytes and Macrophages," Journal of Virology, vol. 68, No. 9, Sep. 1994.
"Multi-branched peptides based on the HIV-1 V3 loop consensus motif inhibit HIV-1 and HIV-2 infection in CD4+ and CD4 cells," C.R. Acad. Sci. Paris, Life sciences, vol. 316, No. 11, Nov. 1993.
"PO5, a New Leiurotoxin I–like Scorpion Toxin: Synthesis and Structure–Activity Releationships of the α–Amidated Analog, a Ligand of $Ca^{2+}$–Activated $K^+$Channels with Increased Affinity," Biochemistry, vol. 32, No. 11, 1993.
"Synergistic Inhibition of HIV–1 Envelope–Mediated Cell Fusion by CD4–Based Molecules in Combination with Antibodies to gp120 or gp41," AIDS Research and Human Retroviruses, vol. 9, No. 7, 1993.
"Solid Phase Synthesis," Science, vol. 232, 18 Apr. 1986.
Tam, J. (1988) Synthetic peptide vaccine design: Synthesis and properties of a high–density multiple antigenic peptide systim. Proc Natl. Acad. Sci. USA 85, 5409–5413. See entire article.
Lehninger, A. L. Principles of Biochemistry, Worth, NY, 1982, p. 98.
Lane, H. et al. (1985) Immunologic Reconstitution in the Acquired Immunodeficiency Syndrome. Ann. Int. Med. 103, 714–718. See entire article.

Primary Examiner—Christine M. Nucker
Assistant Examiner—Jeffrey Stucker
Attorney, Agent, or Firm—Chilton, Alix & Van Kirk

[57] ABSTRACT

The present invention teaches multiple branch peptide constructions (MBPCs) formed from a core matrix to which is attached peptides derived from the V3 loop of the envelope glycoprotein of HIV-1, and including the amino acid sequence GPGR (SEQ ID NO: 5), preferably in the form GPGRAF, but which peptides preferably are free of the amino acid sequences IGPGR (SEQ ID NO: 1) or IXXG-PGR (SEQ ID NO: 3), where X is an amino acid residue, and the use of such MBPCs as a therapy against HIV. The MBPCs prevent virus/cell infection and cell-to-cell virus transmission between $CD4^+$ cells and HIV without hindering the immunogenic role of the $CD4^+$ cells. Moreover, the MBPCs are effective in blockading both CD4 receptors on lymphocytes and macrophages and GalCer receptors on colon epithelial cells. These MBPCs are not immunogenic nor toxic at doses of their intended use (<[$10^{-3}$M]), thus allowing for them to be used therapeutically.

27 Claims, 9 Drawing Sheets

Figure 1

1) Binding step: interaction of the envelope glycoprotein with the CD4 binding site (CDR2 region)

2) Post-binding event: V3 loop interaction with the CD4 fusion domain (CDR3 region)

Inhibition of the V3 loop binding to:
A) the CD4 fusion domain (blockage of the fusion process)
B) the GalCer receptor

Interaction of the envelope glycoprotein V3 loop with the GalCer binding site

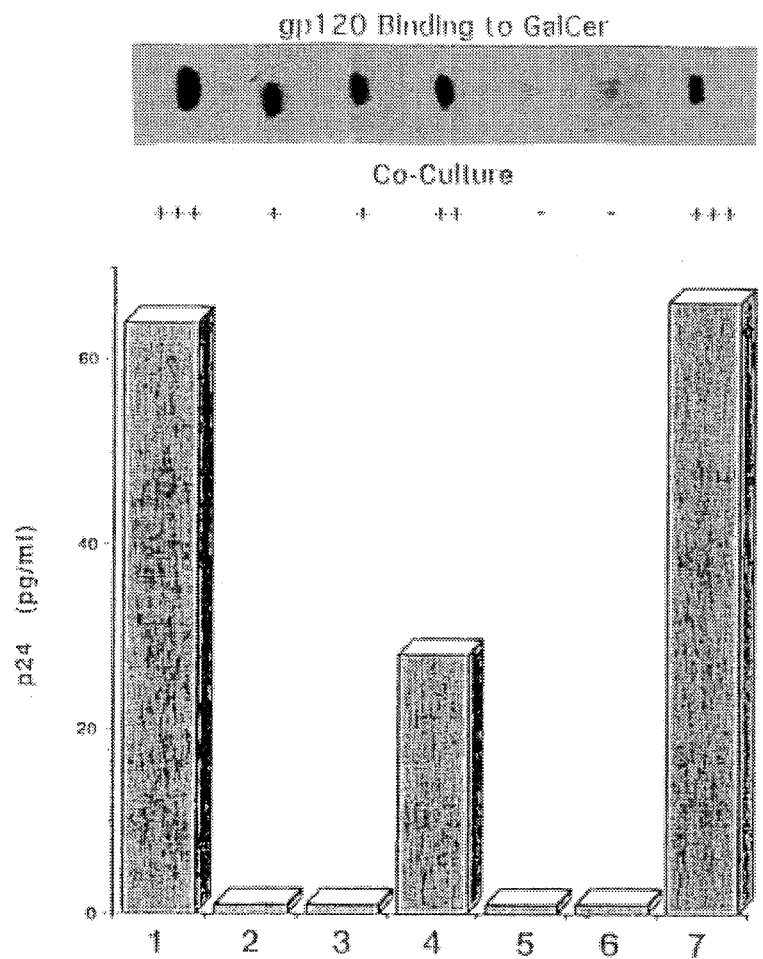

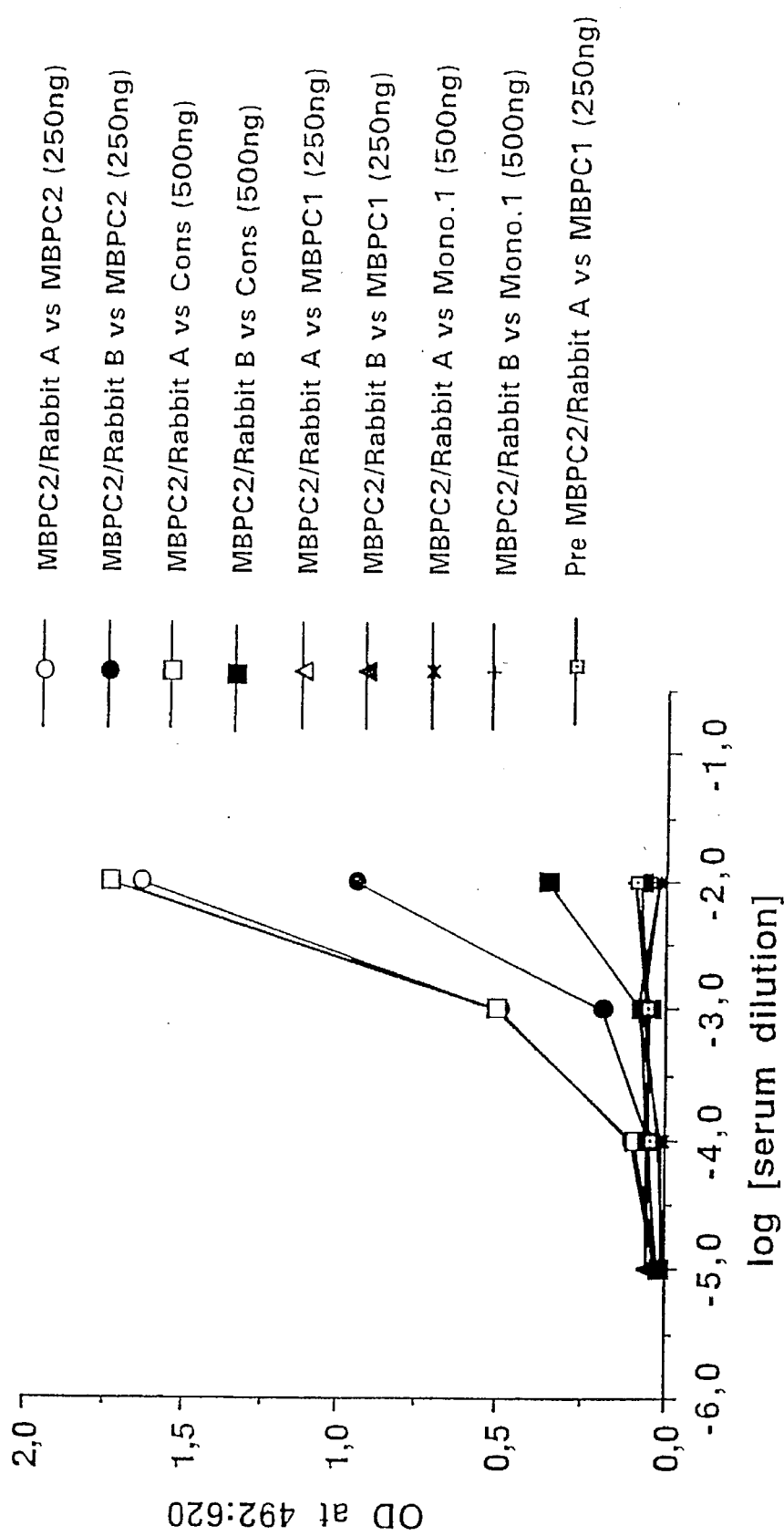
Figure 6A. Immunoreactivity of anti-MBPC2 antibodies against MBPC2, MBPC1, Mono.1, Cs Immunoreactivity of anti-MBPC1 antibodies against MBPC1, Mono.1, Cs, MBPC2

OD at 492:620

OD at 492:620

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Ile Gly Pro Gly Arg
1               5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Gly Pro Gly Arg
1

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Ile Xaa Xaa Gly Pro Gly Arg
1               5

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Arg Lys Ser Ile His Ile Gly Pro Gly Arg Ala Phe Tyr Thr
1               5                   10

-continued ( 2 ) INFORMATION FOR SEQ ID NO:5:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( x i ) SEQUENCE DESCRIPTION: SEQ ID NO:5:

Gly Pro Gly Arg Ala Phe
1               5

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( x i ) SEQUENCE DESCRIPTION: SEQ ID NO:6:

Arg Ala Phe Val Thr Ile Gly Lys
1               5

( 2 ) INFORMATION FOR SEQ ID NO:7:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1..6
( D ) OTHER INFORMATION: /note= "This is [GPGRAF]-MLC
(Multiple Lysine Core)."

( x i ) SEQUENCE DESCRIPTION: SEQ ID NO:7:

Gly Pro Gly Arg Ala Phe
1               5

MULTIPLE BRANCH PEPTIDE CONSTRUCTIONS FOR USE AGAINST HIV

BACKGROUND OF THE INVENTION

Human Immunodeficiency Virus (HIV) is presumably the etiologic agent of Acquired Immunodeficiency Syndrome (AIDS). HIV establishes a persistent infection in different cell types; many of the cells express an antigen, the CD4 receptor, as a binding site at their surface. In such cells, the first step of cell infection is represented by viral attachment with binding of the external envelope glycoprotein of HIV to the CD4 surface antigen of the cell. This binding is followed by a series of events involving virus envelope and target cell membrane fusion and internalization, through which the cell is infected. HIV infected cells may then infect other cells, forming syncytia (giant polynuclear cells). Syncytia formation between HIV-1 infected cells and uninfected CD4$^+$ cells (cells having the CD4 receptor) involves an interaction between the CD4 receptor and the HIV surface envelope glycoprotein. This process is blocked by soluble CD4, antiCD4 and anti-V3 antibodies.

Cell fusion processes responsible for cell-to-cell spread of the virus in vivo make plasma neutralizing antibodies obsolete and leads to virus escape from the immune system already damaged by lymphocyte depletion. B lymphocytes activated by HIV produce different antibody populations. Some antibodies do not interfere with gp120-CD4 interaction, but block membrane fusion, the process responsible for cell infection. These antibodies are principally directed against the envelope glycoprotein V3 loop.

Due to the very high variability of V3 loop in different HIV-1 isolates, anti-V3 antibodies generally only neutralize the isolate against which the antibodies were produced. Therefore neutralization is limited to that isolate and is called isolate specific. These antibodies are effective by cell fusion inhibition, without any activity on cell-virus binding.

Several attempts have been made to inhibit HIV infection by V3 loop-related peptides raising questions as to the efficacy of such peptides. For example, De Rossi et al. [*Virology* 184, 187–196 (1991)] found that some V3 peptides enhanced viral infectivity. Other synthetic peptides from the V3 loop, cyclic or non cyclic, were ineffective in the critical step of cell fusion. Thus, antagonist peptides have not been developed which are capable of blocking virus-cell fusion and cell-to-cell fusion independently of the virus isolate.

More recently, several studies have demonstrated a CD4 independent route of cell infection for both HIV-1 and HIV-2, suggesting the existence of at least one alternative viral receptor. One of these putative non-CD4 HIV receptors has been recently identified on CD4-brain-derived cells and colon epithelial cells. This receptor is a neutral glycolipid, called galactosyl ceramide (GalCer). HIV infection of CD4$^-$/GalCer$^+$ cells in the brain and in the intestine may account for some of the HIV-associated disorders in these organs. Moreover, the presence of GalCer on the apical side of some mucosal epithelial cells may facilitate the entry of the virus during sexual intercourse. No peptide derived from the V3 loop has yet shown ability to block the GalCer receptor.

In response to some of these problems, radially branched systems using lysine skeletons in polymers have been used by J. P. Tam [*Proc. Natl. Acad. Sci. U.S.A.*, 85, 5409–5413 (1988)] to develop antigens without the use of carriers. Those antigens were designed to generate vaccines against a variety of diseases. Specifically, antigens for generating vaccines against HIV infection are described by Tam in PCT patent application ser. no. W093/03766 and essentially include the sequence IGPGR (SEQ ID NO: 1) (IUPAC convention single letter nomenclature for amino acids) and are of eleven amino acids in length to be effective in eliciting useful immune responses. Id. at page 13, lines 29–31. Such antigens are not, however, considered as potential direct therapeutic approaches to any disease, but are intended to provoke an immunogenic response in the body.

SUMMARY OF THE INVENTION

The present invention includes a method and peptide construction for the therapeutic treatment of patients with HIV infections. In accordance with this method, the multiple branch peptide construction for therapeutic administration comprises a core matrix attached to from 2 to 64 peptides, each comprising the amino acid sequence GPGR preceded by from 0 to 4 amino acid residues and succeeded by from 2 to 4 amino acid residues. The multiple branch peptide construction is administered at a concentration of about $10^{-4}$ molar or less.

BRIEF DESCRIPTION OF THE DRAWINGS

FIG. 1 is a proposed binding mechanism for HIV and CD4$^+$ or CD4$^-$ cells.

FIG. 5A illustrates the effect of MBPCs on human epithelial cell infection through the GalCer receptor.

FIG. 5B illustrates the ability of MBPCs to block the binding of gp120 to the GalCer receptor.

FIGS. 6A, 6B, 7A, 7B and 7C all illustrate the relative non-reactivity of rabbit sera immunized with a short MBPC, as compared to rabbit sera immunized with a longer MBPC.

DETAILED DESCRIPTION OF THE INVENTION

I. Structure

Figures 2A, 2B, 2C:
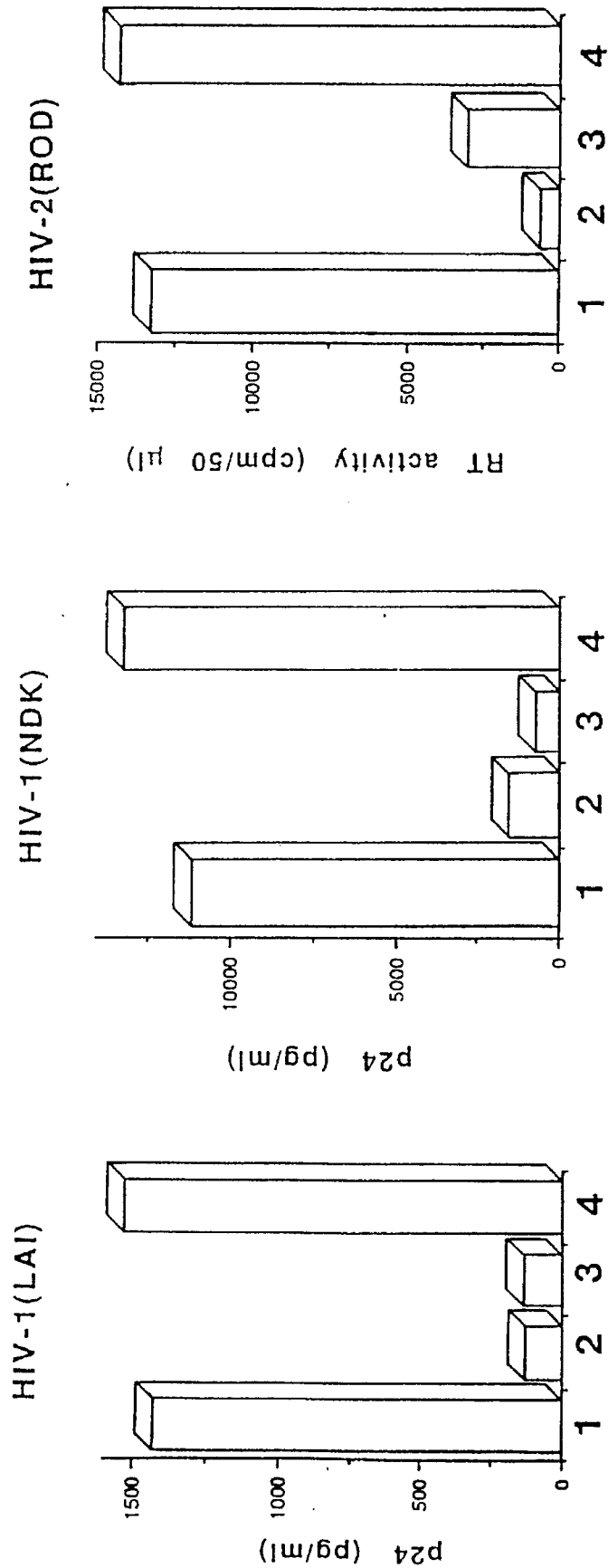
FIGS. 2A–2C show the results of testing the effect of Multiple Branch Peptide Constructions (MBPCs) on the infection of human peripheral blood lymphocytes (PBLs) for three different strains of HIV, with the amount of p24 (pg/ml) or Reverse Transcriptase (RT) activity plotted against three different MBPCs, 1- none; 2- [GPGRAF]$_8$-Multiple Lysine Core (MLC); 3- [RKSIHIGPGRAFYT]$_4$-MLC; 4- [PPYVEPTTTQC]$_4$-MLC.

The present invention relates to Multiple Branch Peptide Constructions (MBPCs) which are able to inhibit HIV infection and the spread and extension of HIV infection. The MBPCs have a core matrix onto which peptides are covalently bonded. The core matrix is a dendritic polymer which is branched in nature, preferably with each of the branches thereof being identical. The core matrix is based on a core molecule which has at least two functional groups to which molecular branches having terminal functional groups are covalently bonded. Suitable core molecules include ammonia or ethylenediamine. Suitable molecular branches include acrylic ester monomers which are polymerized onto the core molecule. Such molecules may be created to present varying number of branches, depending on the number of monomers branched from the core molecule. Contemplated for use herein are MBPCs with 2 to 64 branches and preferably between 4 and 16 branches.

Exemplary for use to form the core matrix is lysine. A central lysine residue is bonded to two lysine residues, each through its carboxyl group, to one of the amino groups of the central lysine residue. This provides a molecule with four amino groups, which may be the core matrix for an MBPC having four peptides. Alternatively, one can provide a molecule with eight branches by bonding four lysine residues through their carboxyl groups to one of the amino groups of the lysine residues which are attached to the central lysine. This molecule can serve as the core matrix for an MBPC having eight peptides or can alternatively receive eight lysine residues to form a core matrix for an MBPC having sixteen peptides. As may readily be seen, larger MBPCs similarly may be constructed as necessitated, having 32 branches.

The C-ends of peptides are covalently bonded to each of the branches of the core matrix to form the MBPC. The peptides may be the same, which is preferred, or may be different from one another. The resulting molecule has a cluster of peptides at the surface and an interior core matrix which is not presented and is therefore not antigenic. For examples of similar structures having peptides different from those contemplated herein, see J.P. Tam [*Proc. Natl. Acad. Sci. U.S.A.*, 85, 5409–5413 (1988)] and U.S. Pat. No. 5,229,490 to Tam and the references cited therein.

Spacers may, if desired, be included between the peptides and the core matrix. The carboxyl group of the first lysine residue may be left free, amidated, or coupled to β-alanine or another blocking compound.

Peptides can include D or L-amino acid residues. D amino acids last longer in vivo because they are harder for peptidase to cut, but the L amino acids have better activity, as discussed below.

Moreover, peptide analogues, synthetic constructs using the carbon skeleton of peptides but omitting the —CONH— peptide bonds, can be employed in place of peptides. Thus, it should be understood that references to peptides herein may also be taken to include peptide analogues. It is believed that peptide analogues will be more resistant to peptidase and last longer in vivo.

The MBPCs of the present invention include peptides derived from the V3 loop of the surface envelope glycoprotein gp120 of the HIV-1 virus, and include the consensus amino acid sequence GPGR (SEQ ID NO: 2) (IUPAC single letter amino acid nomenclature, i.e., Gly-Pro-Gly-Arg) therefrom. Said MBPCs are effective in inhibiting HIV infections in human cell cultures of different cell types. The inhibition appears to be independent from the viral strain, and even to be effective against HIV-2 strains. They, thus, have wholly surprising therapeutic properties.

It should be noted that the corresponding monomer peptides do not have any therapeutic effect. The difference is believed to occur because the core matrix causes the peptide to undergo a conformational change. Specifically and unexpectedly, the two amino acids following the GPGR in the peptide have been found to bend when the GPGR (SEQ ID NO: 2) monomer is attached to the core matrix. Thus, it is preferred that there are at least two amino acid residues succeeding GPGR (SEQ ID NO: 2) in the peptides attached to the core matrix. However, because if the peptide is too long, the MBPC will become antigenic, it is undesirable to have more than four amino acids following the GPGR (SEQ ID NO: 2) sequence and more than four amino acids preceding said sequence. Hence, the peptide will have twelve or less amino acids.

Specific MBPCs showing activity on inhibition of infection by HIV-1 and HIV-2 retroviruses include the following which are set forth using IUPAC notation for amino acids:

TABLE 1

| Exemplary MBPCs | |
| --- | --- |
| MBPC.1: | $(GPGRAFY)_8$-$(K)_4$-$(K)_2$-K-βA-OH or $(GPGRAFY)_8$-$(K)_4$-$(K)_2$-K-βA-NH$_2$ |
| MBPC.3: | $(GPGRAF)_8$-$(K)_4$-$(K)_2$-K-βA-OH or $(GPGRAF)_8$-$(K)_4$-$(K)_2$-K-βA-NH$_2$ |
| MBPC.12: | $(GPGRAF)_{16}$-$(K)_8$-$(K)_4$-$(K)_2$-K-βA-OH or $(GPGRAF)_{16}$-$(K)_8$-$(K)_4$-$(K)_2$-K-βA-NH$_2$ |

The OH terminal shown above on the β-alanine indicates the carboxyl group thereof, with the amino group being attached to the carboxyl group of the lysine residue. The NH$_2$ terminal indicates a modification of the carboxyl group of the β-alanine, to form a carboxamide terminal; the β-alanine is still attached by its amino group to the carboxyl group of the lysine residue. In the examples reported hereinbelow, the OH forms were used.

Although the peptides should contain the consensus sequence GPGR (SEQ ID NO: 2) to possess the desired therapeutic effect, the inclusion of the conformational sequence of an isoleucine before the GPGR (SEQ ID NO: 1), such as IGPGR (SEQ ID NO: 2) or IXXGPGR (SEQ ID NO: 3) (where X is any amino acid residue), also from the V3 loop, has been found to render the MBPC poorly effective or ineffective as a therapeutical treatment when the peptides containing the IGPGR (SEQ ID NO: 1) sequence are of twelve or less amino acid residues and thus are not preferred for use herein. The sequence of an isoleucine (I) being present within three amino acids prior to GPGR (SEQ ID NO: 2) is a relatively conserved one, being found in about 98% of HIV genomes, but, surprisingly, it has been discovered to be undesirable.

Despite MBPCs containing the IGPGR (SEQ ID NO: 1) or IXXGPGR (SEQ ID NO: 3) sequence not being preferred, MBPCs with that peptide sequence have been found to block syncytia formation if the replicated peptide is longer than twelve amino acid residues. For example, one such larger MBPC which does block syncytia formation is that in which the peptide bonded to each branch of a four-branched MBPC is RKSIHIGPGRAFYT (SEQ ID NO: 4). However, such large MBPCs are undesirable because such large molecules have been shown to elicit antibodies, even at low concentrations ($10^{-4}$M), and are recognized and inhibited by HIV infected patients' antibodies, both of which would preclude them from being used in HIV-infected patients over a long term. These MBPCs also show toxicity on cell cultures at concentrations near their effective concentrations. Moreover, the size of these MBPCs makes them very difficult and expensive to fabricate, and more sensitive to protease degradation.

The invention therefore provides an MBPC comprising a core matrix to which are bonded from 2 to 64, and preferably from 4 to 32 peptides, each of which comprises the sequence GPGR (SEQ ID NO: 2) preceded by from 0 to 4 amino acid residues and succeeded by from 2 to 4 amino acid residues. Preferably, the peptides do not contain a sequence of I within three amino acids before G, such as IGPGR (SEQ ID NO: 1) or IXXGPGR (SEQ ID NO: 3), where X is an amino acid residue. Preferably, the peptides bonded to an 8 or 16-branched core matrix are GPGRAF (SEQ ID NO: 5). However, it is believed substitutions are possible in the AF where the substituted amino acids have the same characteristics, and may be desirable because the AF appears to be susceptible to peptidase and therefore, may be fragile in vivo.

II. Preparation of MBPCs

The manufacture of the MBPC structure, that of a branched core with peptides attached thereto, though previously called multiple antigenic peptides (MAPs), has been know in the art. See, e.g., Tam et al., *J. Immun.* 148, 914–920 (1992) and Wang et al., *Science,* 254, 285–288 (1991). Preferably, for small quantities (under one kilogram), a solid phase method is used to obtain the MBPCs. Stepwise assembling of the peptide chains can be carried out automatically on 4-(oxymethyl)-phenylacetamidomethyl copoly(styrene-1% divinyl benzene). The Boc/benzyl strategy may be used, including a systematic double coupling scheme with hydroxybenzotriazole active esters (Boc-amino-acid-OBt). The final cleaving from resin is effected with anhydrous hydrogen fluoride (1 hour at 0° C.). The MBPC is then washed with diethyl ether and solubilized in water. After lyophilization, the MBPC may be pre-purified on a P2 or G15 type molecular filtration column, equilibrated with 0.1N acetic acid. The eluate fraction may then be recovered. The purification step is achieved by using $C_8$ or $C_{18}$ reversed-phase HPLC. The MBPC may be characterized by its amino acid content after acid hydrolysis (6N HCl, 115° C., 24 hours) and electrospray mass spectrometry.

III. Therapeutic Affect and Use

The invention provides a method for the treatment of HIV infections in which there is administered to a patient MBPCs comprising a core matrix to which are bonded from 2 to 64, and preferably from 4 to 32, peptides, each of which comprises the sequence GPGR (SEQ ID NO: 2) preceded by from 0 to 4 amino acid residues and succeeded by from 2 to 4 amino acid residues, but preferably not the sequence IGPGR (SEQ ID NO: 1) or IXXGPGR (SEQ ID NO: 3), where X is an amino acid residue. The MBPCs should be administered at serum levels between $10^{-3}$M and $10^{-7}$M, but preferably at about $10^{-6}$M.

The MBPCs made according to the present invention inhibit both HIV infection and HIV-induced cytopathic effects in vitro, and may therefore inhibit virus multiplication and the spread of the virus in the host organism.

The MBPCs made according to the invention neutralize the virus envelope-cell membrane fusion step, and also the infected cell membrane-uninfected cell membrane fusion step essential for syncytia formation, either step being thought to be indispensable for cell infection, virus multiplication and the spread of virus in the host organism. The MBPCs are able to blockade the CD4 receptor present in cells such as lymphocytes and macrophages, including the 89.6 strain of HIV, apparently by attaching to the CDR3 domain of the CD4 receptor. Thus, the MBPCs of the present invention block the formation of syncytia induced by HIV-1 and HIV-2 and inhibit infection of human peripheral blood lymphocytes (PBLs) and macrophages. Such blocking does not cause the cell to lose its ability to be activated by other antigens or mitogens, that is, the functionality of the lymphocyte is preserved by the MBPCs.

Given the retention of the functionality of the lymphocytes, the potential problem of artificial AIDS is avoided with the present invention. Therefore, that the MBPCs of the present invention attached to the fusion receptor, rather than the receptor for activating the T-cells, is a major advance over any previous therapy against HIV.

In addition to preventing HIV infection, the MBPCs of the present invention have been shown to suppress the production of HIV in cells which have been infected prior to treatment.

One totally unexpected property of the MBPCs of the invention, and especially the preferred 8×GPGRAF (SEQ ID NO: 3) and 16×GPGRAF (SEQ ID NO: 5) MBPCs, is that they have shown an ability to bind to the GalCer receptor which is a receptor for HIV. This receptor has been shown to exist in colon epithelial cells and central nervous system CD4⁻ cells. This binding results in MBPCs inhibiting the infection of human intestinal cells by distantly related isolates of both HIV-1 and HIV-2.

Another advantage of the MBPCs of the present invention is that they have been found to be non-toxic in rodents, rabbits and monkeys at high doses and thus, when used therapeutically will not harm the patient, in contrast to many current AIDS therapies.

Another advantage of the MBPCs of the present invention is that in concentrations of $10^{-4}$M or less they are not immunogenic, and thus, unlike all prior art attempts of using peptides derived from the V3 loop or constructions thereof, are not vaccines. The lack of immunogenicity of the MBPCs is an advantage because an immune reaction would result in antibody production which would inhibit or destroy the MBPCs. Such immunogenic MBPCs, such as the previously mentioned RKSIHIGPGRAFYT (SEQ ID NO: 4), could only be used a few times in the same individual after which it would become ineffective.

A. Blockage of the CD4 Receptor

Experimental data demonstrates a specific inhibitory effect of the MBPCs of the present invention, especially MBPC.3 and MBPC.12, on the process of HIV infection of CD4⁺ cells, and a total blockage of HIV-1 and HIV-2 induced syncytia formation. MBPC concentrations with which inhibiting effects were observed in vitro are around $10^{-6}$M for MBPC.3 and MBPC.12, and at higher concentrations for other MBPCs. The neutralization has been observed on all the HIV strains tested, i.e., MN, Lai, NDK, and 89.6 for HIV-1 and Rod for HIV-2. In contrast, the individual peptide fragments used in the MBPCs are inactive on syncytia formation inhibition, even at very high concentrations, e.g., $5\times10^{-4}$M.

The MBPCs may thus interact with a cellular molecule, involved in a post-binding event, i.e., fusion stage, needed for cellular infection, and used by distantly related HIV-1 and HIV-2 isolates, presenting divergent V3 loops. A good candidate for this postulated V3 binding site is the CDR3 domain of the V1 region of CD4, because: i) anti-CD4 antibodies specific for this region (e.g. 13B8-2) block the fusion process during HIV-1 infection, ii) CDR3-derived synthetic peptides have some inhibitory effect in fusion assays, and iii) MBPCs recognize a synthetic peptide corresponding to the CDR3 domain of CD4.

The MBPCs of the present invention bind to lymphocytes without altering the binding of the viral envelope (through the CDR2 domain), while preventing HIV infecting effects. The MBPCs also bind to the soluble CD4. Therefore, MBPC binding is inhibited in the presence of soluble CD4.

The effect of MBPCs of the present invention on the interaction between region-specific anti-CD4 antibodies and the CD4 receptor in its natural environment was studied. In situ binding of the anti-CDR3 monoclonal antibody (MAb) 13B8-2 to CD4 expressed on macrophages was dramatically and specifically decreased in the presence of MBPCs of the present invention. Binding of other anti-CD4 MAbs, including those recognizing the gp120 binding site (Leu3a and OKT4a mAbs), was identical in the absence and presence of MBPCs. These data demonstrate that MBPCs bind to the CDR3 region of CD4 and thus act, at least in part, by blocking the interaction between the gp120 V3 loop and this domain of CD4.

Despite the V3 loop of HIV-1 being considered to be an important determinant in the fusion process between HIV-1 and its target cells, it has not yet been possible to exploit this property therapeutically until the present invention. The main reason is that V3 is a hypervariable region showing a high degree of diversity among HIV-1 isolates. Neutralizing anti-V3 antibodies are generally type-specific and, in the best case, may neutralize only closely related isolates. Because the MBPCs of the present invention are targeted to cellular and not viral determinants, they by-pass the problems inherent to envelope variability. Thus, the MBPCs used in this invention, although derived from the consensus sequence of the HIV-1 V3 loop, are able to neutralize various HIV-1 strains, including the highly divergent HIV-1 (NDK), and also the unrelated HIV-2 ROD strain. Surprisingly, the MBPCs of the present invention have also been found to inhibit infection with primary HIV-1 isolates, i.e., directly collected from patients, including strains that are resistant to AZT, e.g., J-1.

The following examples, which are not intended to limit the foregoing, illustrate the efficacy, utility and breadth of use of MBPCs of the present invention with regard to HIV infection, and their binding and fusion with $CD4^+$ lymphocytes and macrophages.

EXAMPLE 1

Syncytia Formation Blockage

Cells were cultured in RPM1 1640 supplemented with 5% fetal calf serum, 1% glutamine, 1% streptomycin-penicillin (Gibco of Irvine, Scotland) in a humidified atmosphere with 5% $CO_2$. CEM or C8166 cells were chronically infected with HIV-1 Lai or HIV-2 Rod, or HIV-1MN, respectively. Infected cells ($1 \times 10^4$) were incubated for 2 hours with various concentrations of MBPCs in 96-well plates. Uninfected Molt-4 cells ($4 \times 10^4$) were then added in of culture medium. Syncytia were counted after 18 hours at 37° C. Results are shown in the following Table.

TABLE 2

| MBPC | MBPC Conc. | Syncytia formation | | |
|---|---|---|---|---|
| | | HIV-1MN | HIV-1Lai | HIV-2Rod |
| MBPC.3 | $5 \times 10^{-6}$M | − | − | − |
| | $10^{-6}$M | + | + | − |
| | $10^{-7}$M | +++ | +++ | + |
| MBPC.5 | $5 \times 10^{-6}$M | − | − | − |
| | $10^{-6}$M | ++ | + | − |
| | $10^{-7}$M | +++ | +++ | + |

TABLE 2-continued

| MBPC | MBPC Conc. | Syncytia formation | | |
|---|---|---|---|---|
| | | HIV-1MN | HIV-1Lai | HIV-2Rod |
| MBPC.4 | $5 \times 10^{-6}$M | ++++ | +++ | ++++ |
| | $10^{-6}$M | ++++ | ++++ | ++++ |
| | $10^{-7}$M | +++ | ++++ | ++++ |
| Mono.3 | $10^{-5}$M | ++++ | ++++ | ++++ |
| | $10^{-6}$M | ++++ | ++++ | ++++ |
| | $10^{-7}$M | ++++ | ++++ | ++++ |

MBPC.4 is $(IGPGRAF)_4-(K)_2-K-\beta A-OH$, Mono.3 is the hexapeptide GPGRAF (SEQ ID NO: 5) and MBPC.5 is the tetradecapeptide MBPC $(RKSIHIGPGRAFYT)_4-(K)_2-K-\beta A-OH$. MBPC 3 is as set forth above. The presence of syncytia is indicated by + signs, allocated in approximate proportion to the quantities counted.

MBPC.3 exhibited an in vitro inhibiting effect on syncytia formation induced by HIV at a concentration of around $10^{-6}$M, and MBPC.5 exhibited an inhibiting effect at a slightly higher concentration. MBPC.12 (results not shown) gave results similar to those of MBPC.3. By contrast, the monomeric version Mono.3 is wholly inactive; this has also been confirmed for Mono.3 at the higher concentration of $10^{-4}$M.

EXAMPLE 2

Prevention of Infection of PBLs $50 \times 10^3$ 8E5 cells chronically infected with a RT-deficient HIV-I (IIIB) isolate, were co-cultivated with $150 \times 10^3$ phytohemagglutinin (PHA) stimulated human peripheral blood lymphocytes (PBLs) in the presence of the indicated peptide in 96-well plates. The MBPCs used are described by the peptides attached, and the number thereof, to a core lysine matrix, which is designated HLC. All amino acids used for this experiment were in dextro form.

Chemical synthesis of MBPCs was performed by the solid phase technique, as described above. The peptide chains were elongated stepwise on 4-(oxy-methyl)-pAM resin using optimized t-butyloxycarbonyl/benzyl chemistry. Amino acid analyses of the purified MBPCs agreed with the deduced amino acid ratios. $[GPGRAF]_8$-HLC was further characterized by electrospray mass spectrometry (experimental $M\tau=5672$ Da).

The number of syncytia was determined after 24 hours of incubation in the continued presence of the peptides and the results are presented in Table 3 below. +++ indicates that the number of syncytia present in the well was similar to control untreated wells; − indicates the total absence of syncytia in the well; ± indicates the occasional presence of few syncytia in the well. Syncytia formation in this test was blocked by anti-CD4 antibodies OKT4A (anti-CDR2) and 13B8-2 (anti-CDR3), consistent with previous reports. The core lysine structures (designated "MLCs") by themselves did not induce syncytia formation in this test. Toxicity was evaluated by either MTT assay (described below) or trypan blue exclusion technique.

TABLE 3

Inhibition of HIV-1 induced cell fusion by MBPCs.

| Peptide | Concentration (M) | | |
|---|---|---|---|
| | $5 \times 10^{-7}$ | $5 \times 10^{-6}$ | $5 \times 10^{-5}$ |
| GPGRAF (SEQ ID NO:5) | +++ | +++ | +++ |
| [GPGRAF]$_8$-MLC | ± | − | − |
| [IGPGRAF]$_8$-MLC | +++ | ± | − |
| [GPGRA]$_8$-MLC | +++ | +++ | +++ |
| [GPGR]$_8$-MLC | +++ | +++ | +++ |
| [GPG(R)$_D$AF]$_8$-MLC | +++ | − | Toxic |
| [GPGRAF]$_8$-MLC$_D$ | +++ | +++ | +++ |
| [Ac-GPGRAF]$_8$-MLC | +++ | +++ | − |
| [RKSIHIGPGRAFYT]$_4$-MLC | +++ | − | Toxic |
| [RKSIHKGPGRAFYT]$_4$-MLC | +++ | − | Toxic |
| [RKSIHTGPGRAFYT]$_4$-MLC | +++ | − | Toxic |
| RAFVTIGK (SEQ ID NO:6) | +++ | +++ | − |

Under these experimental conditions, [GPGRAF]$_8$-MLC at a concentration as low as $5 \times 10^{-7}$M, induced a marked inhibition of syncytia formation, while the corresponding monomeric peptide GPGRAF (SEQ ID NO: 5) was not active over the range of concentration used (up to $5 \times 10^{-5}$M). N-terminal acetylation ([Ac-GPGRAF]$_8$-MLC), addition of an isoleucine (I) residue ([IGPGRAF]$_8$-MLC) and incorporation of D-amino acids in the GPGRAF (SEQ ID NO: 5) sequence resulted in a significant loss of activity. MBPCs with less than 6 residues (i.e., [GPGRA]$_8$-MLC or [GPGR]$_8$-MLC), as well as MBPCs with a non-relevant sequence, did not inhibit cell fusion, demonstrating that the core matrix was not involved in the biological activity.

[RKSIHIGPGRAFYT]$_4$-MLC was able to inhibit syncytia formation, at a concentration of $5 \times 10^{-6}$M. Because the isoleucine residue preceding the GPGRAF motif is highly conserved among HIV-1 isolates, two related constructions were synthesized with a lysine or a threonine residue in place of isoleucine. No significant differences in the antifusion activity of these three constructions were observed. However, it should be noted that [RKSIHIGPGRAFYT]$_4$-MLC and its derivatives induced some toxicity in 8E5 cells when used at a concentration of $5 \times 10^{-5}$M and are therefore undesirable for use in human therapy.

Based on these results, the more potent anti-HIV MBPC appeared to be [GPGRAF]$_8$-MLC. In separate tests this molecule was also able to block the fusion between HIV-1 (LAI), HIV-1 (NDK) or HIV-2 (ROD) chronically infected T-lymphblastoid CEM cells and HTLV-I-transformed MT-2 cells.

EXAMPLE 3

Effect of MBPCs on Lymphocyte Functionality a) Effect of MBPCs on Antigen and Mitogen-Induced Cell Proliferation Peripheral blood lymphocytes (PBL) from 3 healthy HIV sero-negative donors were isolated from heparinized blood by the Ficoll-Hypaque technique. The culture medium was RPMI 1640 supplemented with 1% glutamine, 1% antibiotics and 10% heat inactivated fetal calf serum. Cells ($10^5$) were incubated in the presence of MBPCs ($5 \times 10^{-6}$M) with or without antigen (candidine, PPD) or mitogen (PHA). Antigen or mitogen treated cells were pulsed for eight hours with 1 mCi of [3H] thymidine. Then cells were harvested and [3H] thymidine incorporation in DNA was counted.

b) Mixed Lymphocyte Response (MLR)

In this assay, peripheral blood lymphocytes from the three healthy donors (105) were incubated with 105 cells from a mixture of 10 seronegative donors in 200 µl final volume in the presence or absence of various concentrations of MBPCs in microtitre plate wells. Lymphocyte mixtures were pulsed on day 6 for 8 hours with 1 µCl of [$^3$H]Thymidine. Cells were harvested and [$^3$H]Thymidine incorporation into DNA was counted in a beta counter. The results are shown in Table 4 below with MBPC.5 as set forth in the First test.

TABLE 4

PBL Antigen and Mitogen Induced Proliferation
[$^3$H] Thymidine Incorporation (cpm)

| | control | MBPC.3 | MBPC.5 |
|---|---|---|---|
| Donor 3 | | | |
| PHA1 | 203000 | 162000 | 228000 |
| PHA2 | 183000 | 154000 | 188000 |
| PPD1 | 5900 | 3900 | 4000 |
| PPD2 | 3200 | 3100 | 2400 |
| Cand1 | 3900 | 3200 | 3700 |
| Cand2 | 1700 | 1200 | 1100 |
| Donor 2 | | | |
| PHA1 | 115000 | 87000 | 115000 |
| PHA2 | 112000 | 95000 | 111000 |
| PPD1 | 38000 | 24000 | 24000 |
| PPD2 | 33000 | 27000 | 26000 |
| Cand1 | 28000 | 17000 | 15000 |
| Cand2 | 13000 | 11000 | 9000 |
| Donor 1 | | | |
| PHA1 | ═ | ═ | ═ |
| PHA2 | ═ | ═ | ═ |
| PPD1 | 1200 | 1300 | 1300 |
| PPD2 | 1500 | 3100 | 2100 |
| Cand1 | 74000 | 87000 | 80000 |
| Cand2 | 79000 | 100000 | 85000 |

The thymidine incorporation in cells is similar in treated and control plates. If the functionality of the PBLs had been negatively effected, the incorporation of thymidine a marker of cell reproduction, would be considerably increased in MBPC treated plates. Thus, these results demonstrate that there is no proliferation of PBLs, as is seen when they have lost their ability to respond to antigens or mitogens.

EXAMPLE 4

Effect of MBPCs on the Infection of Human PBLs

Peripheral blood lymphocytes (PBLs) were obtained from healthy donors, stimulated with phytohemagglutinin, and cultivated in RPMI 1640 containing 10% fetal calf serum and interleukin-2 (complete medium). Samples of $6 \times 10^6$ cells/ml were either treated or not treated with the indicated MBPC at a concentration of $10^{-5}$M and exposed to HIV-1 or HIV-2 (100 TCID$_{50}$) for 1 hour at 37° C. in the continued presence of MBPCs. After thorough washing, PBLs were cultured in complete medium with $10^{-5}$M of the corresponding MBPC. The state of infection was assessed by determination of RT activity (for both HIV-1 and HIV-2 isolates) and HIV-1 p24$^{gag}$ measurements (Coulter kit, cut-off 10 pg/ml) in the case of HIV-1 isolates 10 days post-infection. The MBPC treatment used were as follows: 1-none; 2-[GPGRAF]$_8$-MLC; 3-[RKSIHIGPGRAFYT]$_4$-MLC; 4-[PPPYVEPTTTQC]$_4$-MLC (a non-HIV related MBPC) (MLC indicates a core lysine structure). The results shown in FIGS. 2A–2C are representative of three separate experiments. The nature of the viral isolates used was checked by PCR (HIV-1 versus HIV-2 isolates) and RIPA for discriminating between HIV-1 (LAI) and HIV-1 (NDK).

[GPGRAF]$_8$-MLC and [RKSIHIGPGRAFYT]$_4$-MLC treatment consistently caused a delay in the production of virus progeny as assessed by the measurement of reverse transcriptase (RT) activity in the culture supernatants: at days 10 and 13 after infection, RT activity was more than 90% lower in MBPCs-treated samples than control samples. Since the peptides did not interfere with the RT assay, this is consistent with a MBPC induced inhibition of viral production. Similar results were obtained (for HIV-1 isolates) when viral production was followed by determination of p24$^{gag}$ concentration in the culture supernatant. [RKSIHIGPGRAFYT]$_4$-MLC was less potent than [GPGRAF]$_8$-MLC for inhibition of HIV-2 infection. MBPCs which did not contain a consensus sequence from the V3 loop did not inhibit infection of PBLs.

EXAMPLE 5

MBPC Inhibition of Syncytia Formation in Macrophages

Figure 3:
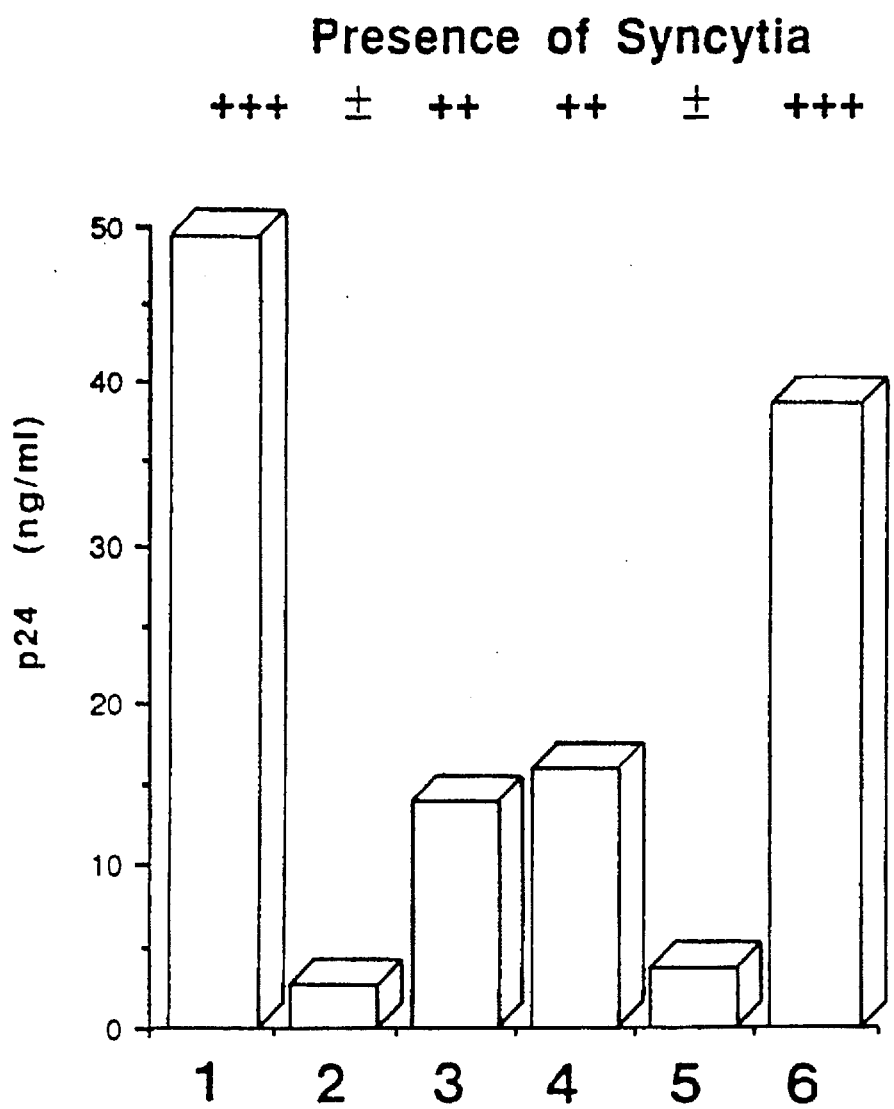
FIG. 3 are the results of testing the MBPCs on human macrophage infection with the MBPCs plotted against the amount of p24 (ng/ml). Five different MBPCs are used: 1- none; 2- [GPGRAF]$_8$-MLC; 3- [GPGRAF]a-MLC$_D$; 4- [GPG (R)$_D$AF]$_8$-MLC; 5- [RKSIHIGPGRAFYT]$_4$-MLC; and 6- [PPYVEPTTTQC]$_4$-MLC.

MBPCs were also evaluated for their ability to block the infection of human primary macrophages by a highly cytopathic macrophage-tropic isolate, HIV-1 (89.6). Mononuclear cells were isolated from leukophoresis units enriched for monocytes by Ficoll-Hypaque density separation. Macrophages were purified by adherence to plastic in RPMI 1640 supplemented with 10% fetal calf serum and 5% human AB serum. The adherent cells were cultured for 5 days in the presence of GM-CSF (1 ng/ml) and were positive for the human macrophage marker (Boehringer Mannheim, clone 25F9). 5×10$^5$ cells were treated for 45 minutes with the indicated MBPC at concentrations of 5×10$^{-5}$M and subsequently exposed to 10,000 TCID$_{50}$ of the macrophage-tropic isolate HIV (89.6). The MBPCs used were as follows: 1-none; 2- [GPGRAF]$_8$-MLC$_D$; 4- [GPG(R)DAF]$_8$-MLC; 5- [RKSIHIGPGRAFYT]$_4$-MLC; 6- [PPPYVEPTTTQC]$_4$-MLC, with amino acids being in L form unless noted as being in D form. After thorough washing, the cells were fed again with medium and analyzed for HIV-1 p24$^{gag}$ production and syncytia formation 4 days post-infection. The results are depicted in FIG. 3 with the MBPCs plotted against the amount of p24 (ng/ml). As also indicated in FIG. 3 the relative number of syncytia per well (+++, no inhibition; ++, 50% inhibition; ±, >95% inhibition) correlated with the concentration of p24$^{gag}$.

Figures 4A, 4B:
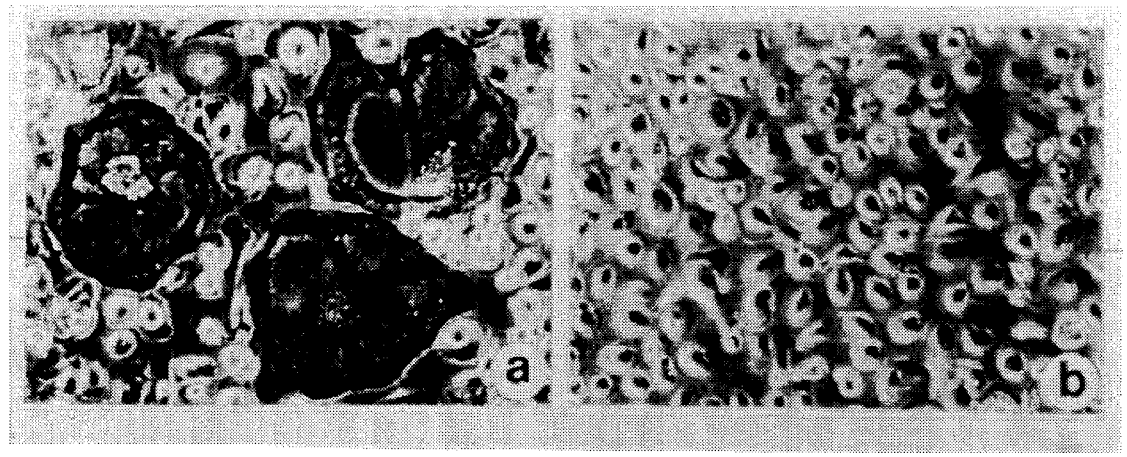
FIG. 4A depicts syncytia formation in infected cultures without any MBPCs.
FIG. 4B depicts the absence of syncytia formation in macrophages treated with [GPGRAF]$_8$-MLC.

Macrophages depicted in FIG. 4A are untreated controls and show the presence of numerous syncytia in infected cultures. Macrophages as depicted in FIG. 4B at a 100×, which were pretreated with [GPGRAF]$_8$-MLC, displayed very few giant cells. [RKSIHIGPGRAFYT]$_4$-MLC and [GPGRAF]$_8$-MLC were able to inhibit infection, as assessed by i) the large decrease of visible cytopatic effects in macrophage cultures exposed to 10,000 TCID$_{50}$ of HIV-1 (89.6) in the presence of MBPCs and, ii) the measurement of HIV-1 p24$^{gag}$ concentration and RT activity in the culture supernatants. Control MBPCs did not significantly affect the infection rate of macrophages by HIV-1 (89.6). Interestingly, [GPGRAF]$_8$-MLC$_D$ (i.e., [GPGRAF]-MLC (SEQ ID NO: 7) with D-amino acid residues) and [GPG(R)$_D$AF]$_8$-MLC were significantly less active than [GPGRAF]$_8$-MLC on macrophage infection.

B. GalCer Receptor

The MBPCs of the present invention, especially MBPC.3 and MBPC.12 and their derivatives, also bind to the second receptor, Galactosyl Ceramide receptor, (see Harouse et al., Science, 253, 320–323 (1991)), and completely block the infectivity of HIV on human colon cells. The corresponding monomeric peptides are inactive on this receptor.

To obtain a total blockage of the GalCer pathway of infection in intestinal cells using the GPGRAF (SEQ ID NO: 5) peptide in the MBPC, the degree of polymerization of the MBPC must be at least 8. This suggests that the conformational requirement of the V3 loop for GalCer recognition is more stringent than for binding to the CDR3 domain of CD4. CDR3 is an acidic region (comprising a glutamic acid residue at position 87 which has been reported to be essential for the fusion process), which probably interacts with basic amino acids of the V3 loop by electrostatic interactions. In contrast, the galactose head group of GalCer, which is known to be involved in gp120 binding, is neutral polar and may require a different spatial arrangement of atoms in the V3 structure for optimal interaction. Thus, it is surprising that a therapy for blocking CD4 route HIV infection would also function with the GalCer receptor.

The activity of MBPCs was evaluated on this alternative infection route as follows: HT-29 cells (5×10$^5$ cells) were incubated with MBPCs (5×10$^{-6}$M) for 45 minutes and subsequently exposed to 100 TCID$_{50}$ of HIV-1 (LAI), HIV-1 (NDK) or HIV-2 (ROD) for 1 hour at 37° C. The residual inoculum was inactivated by three successive trypsinations and infection was assessed by: i) direct measurement of HIV-1 p24$^{gag}$ (for HIV-1 isolates) and RT activity (for HIV-1 and HIV-2 isolates) in the culture supernatants; ii) co-cultivation with human PBLs. The cells were treated with the MBPCs as follows: 1- none; 2- [GPGRAF]$_8$-MLC; 3- [GPGRAF]$_8$-MLC$_D$; 4- [GPG(R)DAF]$_8$-MLC; 5- [GPGRAF]$_{16}$-MLC; 6- [RKSIHIGPGRAFYT]$_4$-MLC; and 7- [PPPYVEPTTTQC]$_4$-MLC, with all amino acids in L form unless noted otherwise. The results shown in FIG. 5A, which correspond to infection with HIV-1 (NDK), are representative of three separate experiments and the MBPC used is indicated by the number on the x-axis. The concentration of p24$^{gag}$ (pg/ml) was measured during the co-culture experiment with PBLs (+++, >10 ng/ml 10 days post-infection; ++, >1 ng/ml 13 days post-infection; +, >1 ng/ml 16 days post-infection; −, no detectable p24$^{gag}$ 1 month post-infection). Similar results were obtained with HIV-1 (LAI) and HIV-2 (ROD).

In another experiment with the same MBPCs, the effect of MBPCs on the binding of gp120 to GalCer was analyzed using a high performance thin layer chromatography (HPTLC) binding assay. MBPCs (10$^{-4}$M) were preincubated with GalCer for 1 hour at room temperature. After thorough washing, the HPTLC plates were incubated with HIV-1 recombinant gp120 (2.5 ug/ml) followed by rabbit anti-gp120 and $^{125}$I-goat anti-rabbit IgG. The plates were washed in PBS and exposed to Amersham Hyperfilm MP for 8 hours. As shown in FIG. 5B treatment of HT-29 cells with active MBPCs protected the cells from infection by HIV-1 (NDK isolate). This antiviral effect was correlated with its ability to block the binding of gp120 to GalCer. Neither monomeric V3 peptides nor control MBPCs displayed any antiviral activity and did not inhibit gp120 binding to GalCer.

The invention therefore additionally provides an MBPC comprising a core matrix to which are bonded from 2 to 64 (preferably from 4 to 32) peptides, each derived from the V3 loop of the surface envelope glycoprotein gp120 of the HIV-1 virus, the FIBPC being capable of inhibiting the infectivity of the HIV viruses, in both CD4$^+$/GalCer$^-$ and CD4$^-$/GalCer$^+$ cells.

C. Antigenicity, Toxicity and Immunogenicity

MBPCs of the present invention are not toxic to human PBLs in vitro or in vivo to mice repeatedly injected either intraperitoneally, intravenously or subcutaneously with MBPCs at a concentration of $10^{-3}$M. Mice receiving repeated doses of 1 mg of MBPCs, intraperitoneally and intravenously, have not shown any adverse effects. Additionally, monkeys (macaca sylvana) injected intravenously once, then subcutaneously, every day with doses of 5 mg/kg have not shown any sign of toxic effects after thirty days. Additionally, rabbits and mice injected with [GPGRAF]$_8$-MLC did not produce significant titers of anti-GPGRAF antibodies, in agreement with the concept that MBPCs with less than 10 amino acids residues in each branch of the peptide are not immunogenic at concentration of less than $10^{-3}$M, the intended concentrations of use. Moreover, in vitro, the PBLs retain the ability to be activated by other antigens or mitogen.

1. Antigenicity

Enzyme Linked Immunosorbent Assay (ELISA) of MBPC Immunogenicity

MBPC.1, MBPC.2 and monomeric V3 consensus peptide were tested in ELISA for their immunoreactivities against HIV-1+ sera or HIV-1− sera. For this test MBPC.2 is (RKSIHIGPGRAFYT)$_4$-(K)$_2$K-βA-OH and MBPC.1 is (GPGRAF)$_8$-(K)$_4$-(K)$_2$-K-βA-OH. The positivity of sera was first confirmed by Western Blot analysis using NEW LAV-BLOT Kit (Diagnostic Pasteur) for the detection of anti-HIV-1 antibodies in serum/plasma. Ninety six well microtiter plates were coated with 500 ng/well of peptides. After saturation and washing, 50 μl of HIV-1+ serum (1/100 dilution) were added for 2 hr at 37° C. Staining was performed with peroxidase-coupled swine anti-rabbit IgG. 30 HIV-1 positive sera and 3 HIV-1 negative sera were comparatively analyzed in ELISA assay against V3 peptide derived from the North American/European consensus (V3 Cons) sequence and V3 MBPCs. The results are set forth in Table 5 below.

Of the 30 HIV-1 positive sera: 26 react strongly with V3 Cons and with MBPC.2, one reacted weakly with both peptides, one reacted selectively with MBPC.2, and two sera did not react with any of the peptide.

Interestingly MBPC.1 did not react with any of the HIV-1 positive sera. As compared to MBPC.2, MBPC.1 has been shown to be more effective in blocking HIV-1 and HIV-2 infection and less toxic. The fact that MBPC.1 is not recognized by HIV-1 positive sera may suggest that such MBPC could not interfere with the neutralizing activity of anti-V3 antibodies. Therefore they could act in synergy to neutralize HIV-1 infection.

TABLE 5

| Serum No. | Western Blot HIV-1 | ELISA V3 Consensus | 500 ng of peptide/wall MBPC2 | MBPC1 |
|---|---|---|---|---|
| 1 | + | +++++ | +++++ | − |
| 2 | + | +++++ | +++++ | − |
| 3 | + | +++++ | +++++ | − |
| 4 | + | +++++ | +++++ | − |
| 5 | + | +++++ | +++++ | − |
| 7 | + | +++++ | +++++ | − |
| 8 | + | +++++ | +++++ | − |
| 9 | + | +++++ | +++++ | − |
| 10 | + | +++++ | +++++ | − |
| 11 | + | +++++ | +++++ | − |
| 12 | + | +++++ | +++++ | − |
| 13 | + | +++++ | +++++ | − |
| 14 | + | ++ | ++ | − |
| 15 | + | +++++ | +++++ | − |
| 16 | + | +++++ | +++++ | − |
| 7 | + | +++++ | +++++ | − |
| 18 | + | +++++ | +++++ | − |
| 19 | + | +++++ | +++++ | − |
| 20 | + | − | − | − |
| 21 | + | + | + | − |
| 22 | + | − | − | − |
| 23 | + | − | + | − |
| 24 | + | +++++ | +++++ | − |
| 25 | + | +++++ | +++++ | − |
| 26 | + | +++++ | +++++ | − |
| 27 | + | +++++ | +++++ | − |
| 28 | + | +++++ | +++++ | − |
| 29 | + | +++++ | +++++ | − |
| 30 | + | +++++ | +++++ | − |
| 31 | − | − | − | − |
| 32 | − | − | − | − |
| 33 | − | − | − | − |

2. Toxicity

An MTT assay, a colorimetric cell viability assay using 3-[4,5-Dimethylthiazol-2-yl] 2,5-diphenyltetrazolium bromide, was used to assess the effect of MBPCs on cell viability. CEM or C8166 cells (5×10$^4$) were cultured continuously (15 days) in the presence of various concentrations of MBPCs in the wells of 96-well microtiter plates in 200 μl final volume of RPMI 1640 medium supplemented with 5% fetal calf serum, 1% glutamine, 1% streptomycin-penicillin (available from Gibco of Irvine, Scotland) in a humidified atmosphere with 5% CO$_2$. Every 3 to 4 days, an MTT assay was performed on 100 μl of cells suspension and MBPC were added to cell culture and the volume completed to 200 μl. [GPGRAF]$_8$-MLC, at concentrations of $10^{-7}$ to $10^{-4}$M, was not toxic to cells in this test. Other results are shown in Table 3 above. As indicated the tetradecapeptide MLC which includes the IGPGR sequence is toxic and therefor not appropriate for therapeutic use as contemplated herein.

3. Antigenicity—Immunogenicity Studies on MBPCs

Four C57/BL6 black mice were injected daily for 36 days with 250 μl of MBPC.3 at 4 mg/ml (1 mg). The injection route was intraperitoneal. The blood samples were collected by sub-orbital eye punction. The blood samples were left for 1 hour at 37° C., then overnight at 4° C., and the supernatants (serum samples) thus obtained were separated from the pellets. Sera were tested by ELISA, looking for specific anti-MBPC3 antibody.

Additionally, two New Zealand rabbits were immunized with [GPGRAF]$_8$-MLC: 400 μg of [GPGRAF]$_8$-MLC in 1 ml of PBS, pH 7.4, were mixed with an equal volume of complete Freund's adjuvant and injected intradermally to each rabbit on day 0. This procedure was repeated subcutaneously with incomplete Freud's adjuvant on days 30, 60, 90 and 120. Sera were tested by ELISA, looking for specific anti MBPC.3 antibodies. Data presented here is from the last serum samples (120+7 days).

96-well microtiter plates (Nunc, Rotskild, Denmark) were coated for 2 h at 37° C. with various concentrations of [GPGRAF]$_8$-MLC (500 to 25 ng of [GPGRAF]$_8$-MLC in 50 µl of PBS), pH 7.4, per well. After saturation with 400 µL of casein (5 g/100 ml), different serum dilutions were added for 2 hours at 37° C. The controls were sera from non-immunized rabbits and mice. After rinsing (5×), 50 µl of 1:5000 of peroxidase-labeled swine anti-rabbit IgG or anti-mouse IgG (Dakopatts, Copenhagen, Denmark) were added for 1 hour at 37° C. After further rinsing (5×), 100 µl of orthophenylenediamine were added for 30 min in the dark at room temperature. The reaction was stopped by adding 50 µl of 4N sulfuric acid, and optical density (OD) ratios were determined at 492/620 nm.

Tables 6–10 below set forth the results, with Table 6 setting forth a summary of the results achieved with the rabbits using optical density ratios (×10$^3$). Mo is the GPGRAF (SEQ ID NO: 5) monomer at 10 µg/ml.

TABLE 6

| [GPGRAF]$_8$-MLC (µg/ml) | | serum dilution | | |
|---|---|---|---|---|
| | | 1:10 | 1:100 | 1:1000 |
| 10 | rabbit A | +++ | + | − |
| | rabbit B | + | − | − |
| 5 | rabbit A | +++ | − | − |
| | rabbit B | + | − | − |
| 1 | rabbit A | +++ | − | − |
| | rabbit B | + | − | − |
| 0.5 | rabbit A | + | − | − |
| | rabbit B | − | − | − |

−, optical density (OD) < 0.2; +, OD = 0.2–0.4; ++, OD = 0.4–0.8; +++, OD > 0.8

TABLE 7

| | microtiter plate n° 1 | | | | | | | | | |
|---|---|---|---|---|---|---|---|---|---|---|
| | S 10 | S 10 | S 5 | S 5 | S 1 | S 1 | S.5 | S.5 | Mo | Mo |
| M 10-2 | 1162 | 1199 | 1045 | 933 | 444 | 419 | 382 | 381 | 1224 | 1135 |
| M 10-3 | 339 | 291 | 285 | 236 | 126 | 111 | 128 | 135 | 310 | 287 |
| M 10-4 | 172 | 138 | 121 | 132 | 50 | 51 | 56 | 38 | 104 | 185 |
| M ctrl | 622 | 550 | 527 | 551 | 337 | 313 | 360 | 341 | 516 | 591 |
| R ctrl | 1062 | 1093 | 986 | 976 | 631 | 662 | 621 | 616 | 945 | 989 |
| R 10-2 | 2000 | 2000 | 2000 | 2000 | 1280 | 1267 | 968 | 981 | 2000 | 2000 |
| R 10-3 | 2000 | 2000 | 2000 | 2000 | 346 | 349 | 318 | 296 | 2000 | 2000 |
| R 10-4 | 924 | 823 | 796 | 809 | 182 | 193 | 145 | 140 | 677 | 725 |

Legend:
S 10 = 10 µg MBPC.3/ml; s 5 = 5 µg MBPC.3/ml
S 1 = 1 µg MBPC.3/ml; S.5 = 0.5 µg MBPC.3/ml; Mo = GPGRAF monomer, 10 µg/ml
M 10-2 = [10$^{-2}$] Mouse; R 10-2 = [10$^{-2}$] Rabbit
M ctrl = [10$^{-2}$] non immun. mouse; R ctrl = [10$^{-1}$] non immun. rabbit

TABLE 8

| | microtiter plate n° 2 | | | | | | | | | |
|---|---|---|---|---|---|---|---|---|---|---|
| | S 10 | S 10 | S 5 | S 5 | S 1 | S 1 | S.5 | S.5 | Mo | Mo |
| M 10-2 | 1540 | 1457 | 1514 | 1344 | 381 | 429 | 315 | 841 | 1539 | 1575 |
| M 10-3 | 334 | 291 | 263 | 273 | 54 | 65 | 47 | 82 | 342 | 335 |
| M 10-4 | 132 | 188 | 88 | 97 | 15 | 17 | 13 | 83 | 95 | 126 |
| M ctrl | 490 | 464 | 385 | 231 | 241 | 289 | 235 | 851 | 482 | 500 |
| R ctrl | 437 | 429 | 386 | 345 | 214 | 185 | 117 | 153 | 376 | 395 |

TABLE 8-continued

| | microtiter plate n° 2 | | | | | | | | | |
|---|---|---|---|---|---|---|---|---|---|---|
| | S 10 | S 10 | S 5 | S 5 | S 1 | S 1 | S.5 | S.5 | Mo | Mo |
| R 10-2 | 2000 | 2000 | 2000 | 2000 | 1922 | 87 | 34 | 716 | 2000 | 2000 |
| R 10-3 | 2000 | 2000 | 2000 | 2000 | 394 | 87 | 197 | 181 | 2000 | 1909 |
| R 10-4 | 734 | 689 | 678 | 626 | 113 | 84 | 80 | 74 | 588 | 625 |

Legend:
S 10 = 10 μg MBPC.3/ml; S 5 = 5 μg MBPC.3/ml
S 1 = 1 μg MBPC.3/ml; S .5 = 0.5 μg MBPC.3/ml; Mo = GPGRAF monomer, 10 μg/ml
M 10-2 = $[10^{-2}]$ Mouse; R 10-2 = $[10^{-2}]$ Rabbit
M ctrl = $[10^{-2}]$ non immun. mouse; R ctrl = $[10^{-1}]$ non-immun. rabbit

TABLE 9

| | microtiter plate n° 3 | | | | | | | | | |
|---|---|---|---|---|---|---|---|---|---|---|
| | S 10 | S 10 | S 5 | S 5 | S 1 | S 1 | S.5 | S.5 | Mo | Mo |
| M 10-2 | 639 | 664 | 636 | 630 | 241 | 200 | 204 | 198 | | |
| M 10-3 | 172 | 168 | 159 | 163 | 50 | 53 | 48 | 49 | | |
| M 10-4 | 85 | 84 | 83 | 84 | 22 | 22 | 22 | 21 | | |
| M ctrl | 513 | 492 | 486 | 459 | 257 | 249 | 286 | 261 | | |
| R ctrl | 833 | 238 | 222 | 213 | 92 | 92 | 91 | 88 | | |
| R 10-2 | 818 | 953 | 857 | 868 | 402 | 401 | 416 | 287 | | |
| R 10-3 | 342 | 328 | 323 | 314 | 168 | 150 | 148 | 155 | | |
| R 10-4 | 191 | 184 | 170 | 169 | 72 | 89 | 64 | 69 | | |

Legend:
S 10 = 10 μg MBPC.3/ml; S 5 = 5 μg MBPC.3/ml
S 1 = 1 μg MBPC.3/ml; S .5 = 0.5 μg MBPC.3/ml; Mo = GPGRAF monomer, 10 μg/ml
M 10-2 = $[10^{-2}]$ Mouse; R 10-2 = $[10^{-2}]$ Rabbit
M ctrl = $[10^{-2}]$ non immun. mouse; R ctrl = $[10^{-1}]$ non immun. rabbit

TABLE 10

| | microtiter plate n° 4 | | | | | | | | | |
|---|---|---|---|---|---|---|---|---|---|---|
| | S 10 | S 10 | S 5 | S 5 | S 1 | S 1 | S.5 | S.5 | Mo | Mo |
| M 10-2 | 1454 | 1340 | 1233 | 1336 | 553 | 439 | 495 | 468 | 1231 | 1317 |
| M 10-3 | 334 | 318 | 299 | 297 | 83 | 88 | 90 | 95 | 380 | 386 |
| M 10-4 | 133 | 113 | 124 | 103 | 27 | 21 | 28 | 28 | 123 | 122 |
| M ctrl | 453 | 381 | 349 | 400 | 215 | 235 | 275 | 278 | 468 | 458 |
| R ctrl | 225 | 203 | 285 | 288 | 95 | 86 | 82 | 86 | 283 | 185 |
| R 10-2 | 849 | 843 | 749 | 792 | 419 | 447 | 424 | 425 | 811 | 811 |
| R 10-3 | 332 | 314 | 310 | 304 | 221 | 151 | 163 | 154 | 245 | 194 |
| R ABU | 263 | 279 | 255 | 251 | 105 | 101 | 134 | 128 | 214 | 218 |

Legend:
S 10 = 10 μg MBPC.3/ml; S 5 = 5 μg MBPC.3/ml
S 1 = 1 μg MBPC.3/ml; S .5 = 0.5 μg MBPC.3/ml; Mo = GPGRAF monomer, 10 μg/ml
M 10-2 = $[10^{-2}]$ Mouse; R 10-2 = $[10^{-2}]$ Rabbit
M ctrl = $[10^{-2}]$ non immun. mouse; R ctrl = $[10^{-1}]$ non-immun. rabbit
R ABU = [10-2] rabbit, with peptide Abu (non-related amino acid)

In view of the high amount of background reactivity observed in some of the results, further testing was undertaken to verify the non-reactivity of sera immunized with MBPC.1.

Sera from rabbits immunized with either MBPC.1 or MBPC.2 were tested in ELISA for their ability to bind MBPC.1, MBPC.2, Mono.1 (the monomeric form of MBPC.1) and the North American/European consensus V3 sequence (V3 Cons, or Cs).

Figure 6B:
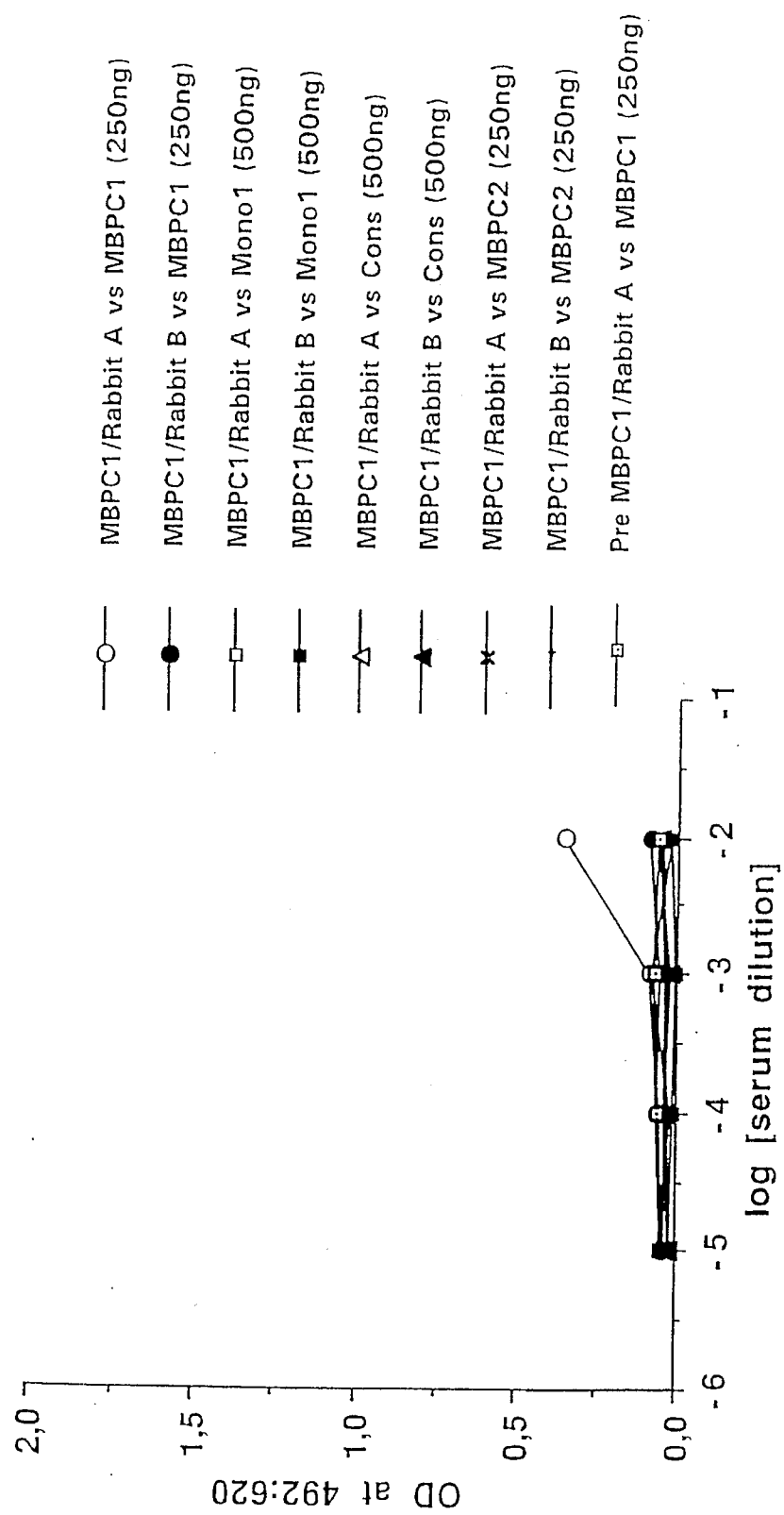

FIG. 6A shows that sera from rabbits immunized with MBPC.2 recognized significantly MBPC.2 and V3 Cons, while no reactivity was observed against MBPC.1 or the corresponding monomeric peptides. FIG. 6B indicates that sera from rabbits immunized with MBPC.1 did not react against MBPC.1 (except for a weak reactivity of the serum from rabbit A), MBPC.2, V3 Cons or Mono.1. Preimmune sera used as negative control likewise did not react against either MBPC, V3 Cons or Mono.1.

Figure 7A:
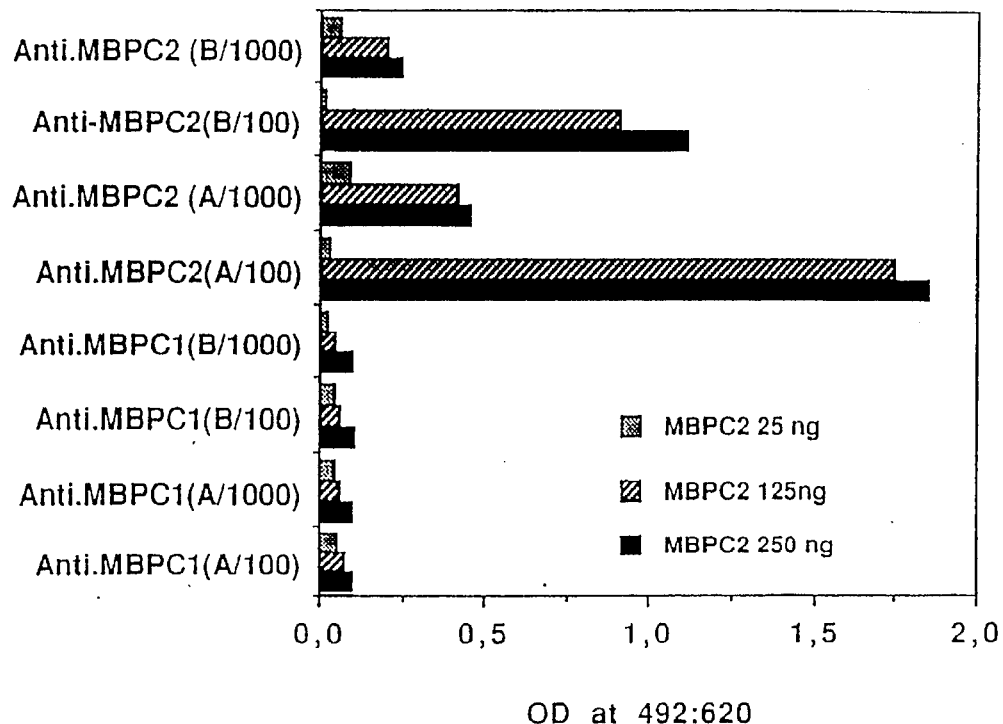
Figure 7B:
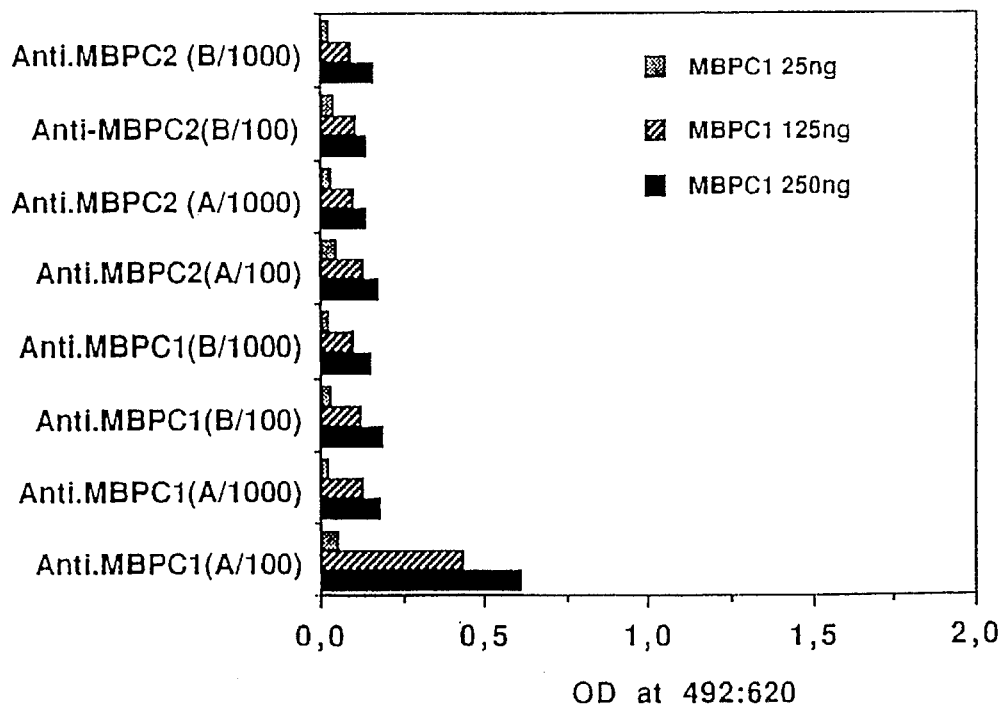
Figure 7C:
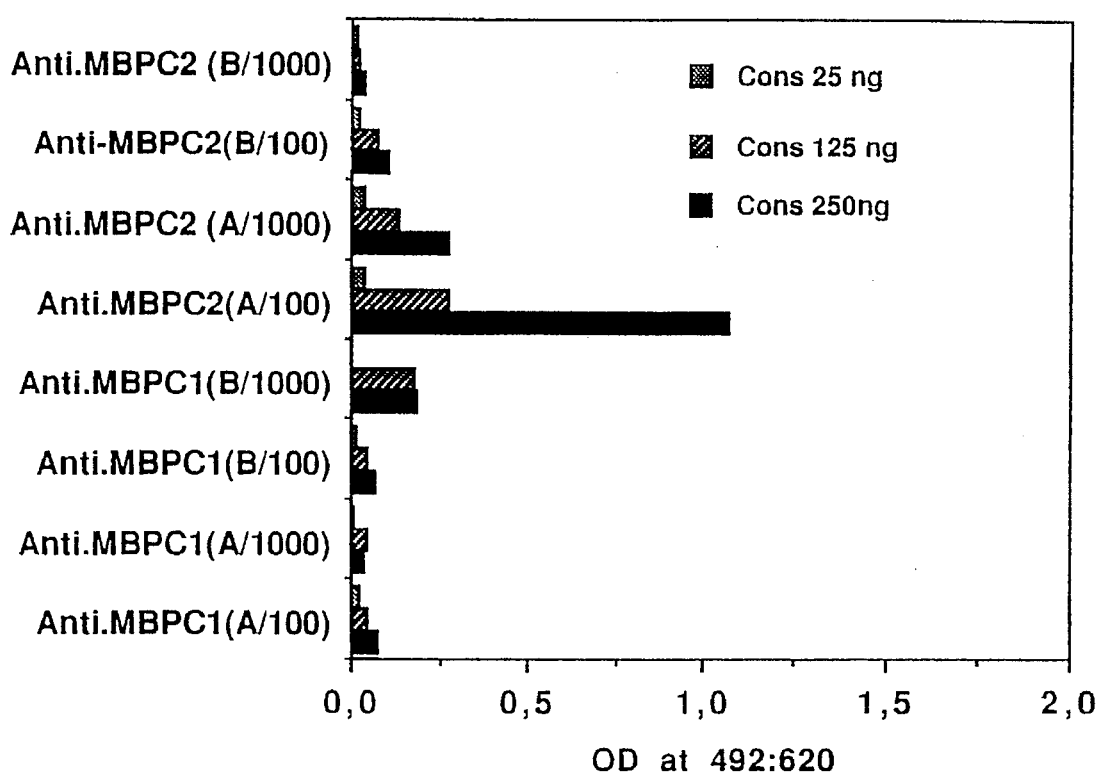

In another set of experiments, sera from rabbits immunized with either MBPC.1 or MBPC.2 were tested (at 1/100 and 1/1000 dilutions) against various concentrations of MBPC.1, MBPC.2 and V3 Cons. FIGS. 7A, 7B and 7C clearly indicate that sera from rabbits immunized with MBPC.2 reacted in a dose dependant manner against MBPC.2 and V3 Cons. No reactivity against MBPC.1 was detected. In contrast, sera from rabbits immunized with MBPC.1 did not react against MBPC.2, while reacting weakly against MBPC.1 (note the weak reactivity of the serum from rabbit A against MBPC.1, with no reactivity of serum from rabbit B). Interestingly, these latter sera did not react with the monomeric V3 Cons, a 34-amino acid linear epitope mimicking the consensus sequence as present on gp120.

These results indicate that MBPC.1, a short V3 MBPC, did not induce a significant antibody response in rabbits, while MBPC.2, the longest V3 peptide construct, did invoke such a response. These observations are in line with the results on the immunoreactivity of MBPC.1 with HIV-1 infected patients' sera.

In mice, repeatedly injected at $10^{-3}$M, very weak titers of antibodies could be occasionally detected in sera at 1:100 dilution, and essentially no antibodies could be detected at lower serum dilutions. In rabbits, antibodies are detectable in one animal at 1:100 serum dilution. At all other serum dilutions, the antibodies titers are comparable to those obtained in control animals. Such weak antigenicity demonstrates that the MBPCs of the present invention do not have the potential to be used as an antigen able to elicit an effective antibody response, which is the use of previously known peptide constructions. Indeed, the intended therapeutic concentrations of the MBPCs of the present invention are around $10^{-6}$M, and no antibody response is expected at such concentrations. However, given the lack of antigenicity the MBPCs may be administered at up to $10^{-3}$M.

We claim:

1. A method of treating HIV infections comprising administering to a patient such amount of a multiple branch peptide construction as is sufficient to induce in the patient a blood concentration of the multiple branch peptide construction of up to $10^{-4}$ molar, the multiple branch peptide construction being non-immunogenic at the aforesaid blood concentration and comprising a core matrix to which are bonded from 2 to 16 peptides which consist of the amino acid sequence GPGR succeeded by from 2 to no more than 4 amino acid residues.

2. A method according to claim 1 wherein from 4 to 12 peptides are bonded to the core matrix of the multiple branch peptide construction.

3. A method according to claim 1 wherein the core matrix is comprised of lysine residues.

4. A method according to claim 1 wherein there are spacers between the core matrix and the peptides.

5. A method according to claim 1 wherein the peptides are peptide analogues.

6. A method according to claim 1 wherein the peptides include at least one D-amino acid residue.

7. A multiple branch peptide construction which at a blood concentration of up to $10^{-4}$ molar is non-immunogenic and which comprises a core matrix to which are bonded 2 to 16 peptides which consist of the amino acid sequence GPGR succeeded by from 2 to no more than 4 amino acid residues.

8. A peptide construction according to claim 7 wherein from 4 to 16 peptides are bonded to the core matrix of the multiple branch peptide construction.

9. A peptide construction according to claim 7 wherein the core matrix is comprised of lysine residues.

10. A peptide construction according to claim 7 wherein there are spacers between the core matrix and the peptides.

11. A peptide construction according to claim 7 wherein the peptides are peptide analogues.

12. A peptide construction according to claim 7 wherein the peptides include at least one D-amino acid residue.

13. A multiple branch peptide construction comprising a core matrix to which are bonded 8 peptides consisting of the amino acid sequence GPGRAF.

14. A peptide construction according to claim 13 wherein the core matrix is composed of lysine residues.

15. A multiple branch peptide construction comprising a core matrix to which are bonded 16 peptides consisting of the amino acid sequence GPGRAF.

16. A peptide construction according to claim 15 wherein the core matrix is composed of lysine residues.

17. A method of treating HIV infections comprising administering to a patient a multiple branch peptide construction comprising a core matrix to which are bonded 8–16 peptides consisting of the amino acid sequence GPGRAF.

18. A method according to claim 17 wherein the multiple branch peptide construction is administered at a concentration of less than $10^{-4}$M.

19. A method according to claim 17 wherein the core matrix is comprised of lysine residues.

20. A composition useful for inhibiting syncytia formation resulting from the fusion of (1) at least one of an envelope of HIV end a cell membrane of an HIV-infected cell to (2) a membrane of an non-HIV-infected cell which has at, least one of a CD4 receptor and a GalCer receptor, the composition containing a multiple-branch peptide construction which comprises a core matrix to which are bonded 2 to 16 peptides which consist of the amino acid sequence GPGR succeeded by from 2 to no more than 4 amino acid residues.

21. A composition according to claim 20, wherein said non-HIV-infected cell is at least one member selected from the group consisting of a peripheral blood lymphocyte, a primary macrophage, and a colon epithelial cell.

22. A composition according to claim 20, wherein there are 8–16 peptides consisting of the amino acid sequence GPGRAF bonded to the core matrix.

23. A composition useful for inhibiting the fusion of (1) at least one of an envelope of HIV and a cell membrane of an HIV-infected call to (2) a membrane of an non-HIV-infected cell which has at least one of a CD4 receptor and a GelCer receptor, the composition being appropriate to induce in a patient a blood concentration of up to $10^{-4}$ molar of a multiple branch peptide construction which comprises a core matrix to which are bonded 2 to 16 peptides which consist of the amino acid sequence GPGR succeeded by from 2 to no more than 4 amino acid residues.

24. A composition according to claim 23, wherein there are 8–16 peptides consisting of the amino acid sequence GPGRAF bonded to the core matrix.

25. A method of inhibiting fusion of (1) at least one of an envelope of HIV and a cell membrane of an HIV-infected cell to (2) a membrane of an non-HIV-infected cell which has at least one of a CD4 receptor and a GelCer receptor, comprising administering to a patient such amount of a multiple branch peptide construction as is sufficient to induce in the patient a blood concentration of the multiple branch peptide construction of up to $10^{-4}$ molar, the multiple branch peptide construction being non-immunogenic at the aforesaid blood concentration and comprising a core matrix to which are bonded from 2 to 16 peptides which consist of the amino acid sequence GPGR succeeded by from 2 to no more than 4 amino acid residues.

26. A method according to claim 25, wherein there are 8–16 peptides consisting of the amino acid sequence GPGRAF bonded to the core matrix.

27. A method according to claim 25, wherein said non-HIV-infected cell is at least one member selected from the group consisting of a peripheral blood lymphocyte, a primary macrophage, and a colon epithelial cell.

\* \* \* \* \*

UNITED STATES PATENT AND TRADEMARK OFFICE
CERTIFICATE OF CORRECTION

PATENT NO. : 5,622,933
DATED : April 22, 1997
INVENTOR(S) : Jean M. Sabatier. et al.

It is certified that error appears in the above-indentified patent and that said Letters Patent is hereby corrected as shown below:

In claim 2, column 21, line 52, delete "12" and insert --16--.

In claim 20, column 23, line 7, delete "end" and insert --and--.

In claim 20, column 23, line 8, delete ",".

In claim 23, column 23, line 23, delete "call" and insert --cell--.

Signed and Sealed this

Seventh Day of October, 1997

Attest:

BRUCE LEHMAN

*Attesting Officer*  *Commissioner of Patents and Trademarks*